US011311728B2

(12) United States Patent
Rozgic et al.

(10) Patent No.: US 11,311,728 B2
(45) Date of Patent: Apr. 26, 2022

(54) ELECTRODE AGNOSTIC, SUPPLY VARIANT STIMULATION ENGINE FOR IMPLANTABLE NEURAL STIMULATION

(71) Applicant: The Regents of the University of California, Oakland, CA (US)

(72) Inventors: Dejan Rozgic, Los Angeles, CA (US); Dejan Markovic, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 117 days.

(21) Appl. No.: 16/479,542

(22) PCT Filed: Jan. 22, 2018

(86) PCT No.: PCT/US2018/014724
§ 371 (c)(1),
(2) Date: Jul. 19, 2019

(87) PCT Pub. No.: WO2018/136886
PCT Pub. Date: Jul. 26, 2018

(65) Prior Publication Data
US 2019/0381316 A1    Dec. 19, 2019

Related U.S. Application Data

(60) Provisional application No. 62/448,853, filed on Jan. 20, 2017.

(51) Int. Cl.
*A61N 1/36* (2006.01)
*A61N 1/05* (2006.01)

(52) U.S. Cl.
CPC ....... *A61N 1/36125* (2013.01); *A61N 1/0531* (2013.01); *A61N 1/0534* (2013.01);
(Continued)

(58) Field of Classification Search
CPC .............. A61N 1/36125; A61N 1/0531; A61N 1/0534; A61N 1/3606; A61N 1/3614; A61N 1/36153
See application file for complete search history.

(56) References Cited

U.S. PATENT DOCUMENTS

| 2004/0021518 A1* | 2/2004 | Wrathall | ............... | H02M 3/156 |
| | | | | 330/253 |
| 2005/0267546 A1* | 12/2005 | Parramon | .............. | A61N 1/025 |
| | | | | 607/48 |

(Continued)

FOREIGN PATENT DOCUMENTS

| WO | 2015139053 A1 | 9/2015 |
| WO | 2018136886 A1 | 7/2018 |

OTHER PUBLICATIONS

International Preliminary Report on Patentability for International Application PCT/US2018/014724, Report issued Jul. 23, 2019, dated Aug. 1, 2019, 6 Pgs.

(Continued)

*Primary Examiner* — Amanda K Hulbert
(74) *Attorney, Agent, or Firm* — KPPB LLP

(57) ABSTRACT

Many embodiments of the invention provide a neuromodulation system that includes a digital control unit (DCU) that activates a stimulation engine during active stimulation, a current mirror that includes two feedback loops including a first feedback loop with positive feedback (PF) made of an error amplifier $A_1$ and transistors $M_3$ and $M_1$ and a second feedback loop with a negative feedback (NF) made of the error amplifier $A_1$ and transistor $M_3$, and a high-voltage adaptive rail ($V_{dd}/V_{ss}$) to accommodate voltage drops across high electrode impedances.

9 Claims, 14 Drawing Sheets

(52) U.S. Cl.
CPC .......... *A61N 1/3606* (2013.01); *A61N 1/3614* (2017.08); *A61N 1/36153* (2013.01)

(56) References Cited

U.S. PATENT DOCUMENTS

| | | | |
|---|---|---|---|
| 2008/0158915 A1* | 7/2008 | Williams | H02M 3/07 363/21.06 |
| 2008/0224761 A1* | 9/2008 | Deng | G05F 3/30 327/539 |
| 2008/0269631 A1 | 10/2008 | Denison et al. | |
| 2013/0338732 A1 | 12/2013 | Foutz et al. | |
| 2014/0277268 A1* | 9/2014 | Lee | H03K 3/023 607/46 |
| 2016/0038739 A1* | 2/2016 | Liu | A61N 1/3616 607/45 |
| 2017/0001003 A1* | 1/2017 | Pivonka | A61N 1/36007 |

OTHER PUBLICATIONS

International Search Report and Written Opinion for International Application No. PCT/US2018/014724, Search completed Mar. 16, 2018, dated Mar. 29, 2018, 12 Pgs.

Ghovanloo et al., "A Wireless Implantable Multichannel Microstimulating System-on-a-Chip With Modular Architecture", IEEE Transactions on Neural Systems and Rehabilitation Engineering, Sep. 2007, vol. 15, No. 3, pp. 449-457, DOI: 10.1109/TNSRE.2007.903970.

Lin et al., "A Battery-Less, Implantable Neuro-Electronic Interface for Studying the Mechanisms of Deep Brain Stimulation in Rat Models", IEEE Transactions on Biomedical Circuits and Systems, Feb. 2016, vol. 10, No. 1, pp. 98-112, DOI: 10.1109/TBCAS.2015.2403282.

Maghami et al., "Analysis and design of a high-compliance ultra-high output resistance current mirror employing positive shunt feedback", International Journal of Circuit Theory and Applications, Dec. 2015, First Published: Dec. 5, 2014, vol. 43, No. 12, pp. 1935-1952, https://doi.org/10.1002/cta.2049.

Ngamkham et al., "Biphasic stimulator circuit for a wide range of electrode-tissue impedance dedicated to cochlear implants", 2012 IEEE International Symposium on Circuits and Systems (ISCAS), May 20-23, 2012, Seoul, South Korea, pp. 1083-1086, DOI: 10.1109/ISCAS.2012.6271417.

Noorsal et al., "A Neural Stimulator Frontend With High-Voltage Compliance and Programmable Pulse Shape for Epiretinal Implants", IEEE Journal of Solid-State Circuits, Jan. 2012, vol. 47, No. 1, pp. 244-256, DOI: 10.1109/JSSC.2011.2164667.

Van Dongen et al., "A Power-Efficient Multichannel Neural Stimulator Using High-Frequency Pulsed Excitation From an Unfiltered Dynamic Supply", IEEE Transactions on Biomedical Circuits and Systems, Feb. 2016, vol. 10, No. 1, pp. 61-71, DOI: 10.1109/TBCAS.2014.2363736.

Yao et al., "A 20V-compliance implantable neural stimulator IC with closed-loop power control, active charge balancing, and electrode impedance check", 2014 IEEE Asian Solid-State Circuits Conference (A-SSCC), Nov. 10-12, 2014, KaoHsiung, Taiwan, pp. 201-204, DOI: 10.1109/ASSCC.2014.7008895.

* cited by examiner

*High Output Impedance Current source and Current sink*

Measured DC Output Characteristic for Current Source and Current Sink

*A) Modified Pellicone stage-NCP; b) Favrat Cell – Positive Pump Stage; c) Unipolar-to-Bipolar High Voltage Level Shifter*

Detailed schematic of reconfigurable BandGap Circuit and Reference Current Sources for Stimulation Engines a) Ceramic SMD Capacitance Drop with DC Voltage; b) Self-resonance frequency of ceramic capacitors; c) Comparison between ceramic SMD and Integrated Passive Capacitances; d) Stacked IPDIA capacitors as a compact energy source, [12].

*Die Micrographs ICs for Electrode Agnostic Stimulation Right" 64 electrodes and 8 STIM Engines; Left 32 electrodes and 4 STIM*

Test Set-Up for STIM Chip and NeuroModulation Assembly In-Vitro Measurement

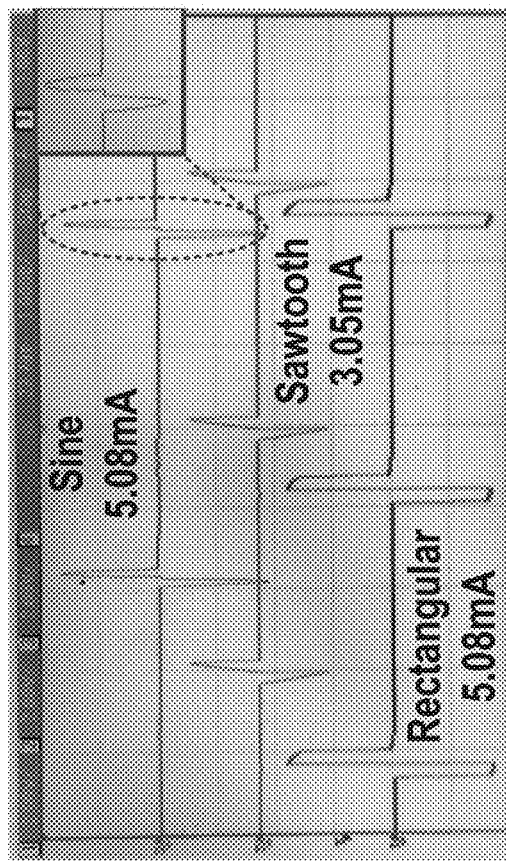
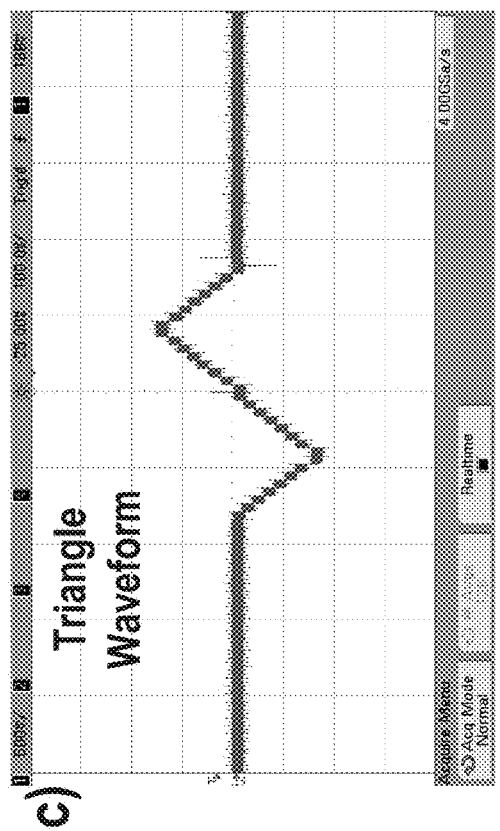
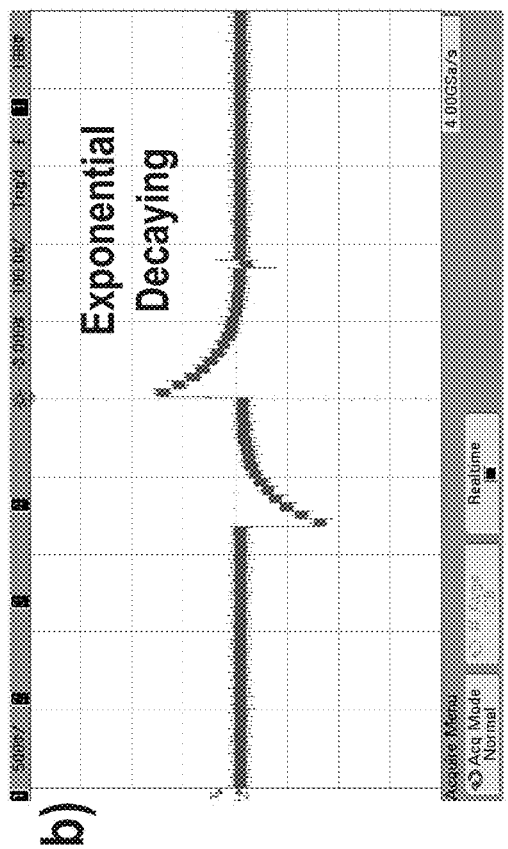
FIG. 14 Measurement Results. Arbitrary Waveforms – Concurrent Stimulation

ELECTRODE AGNOSTIC, SUPPLY VARIANT STIMULATION ENGINE FOR IMPLANTABLE NEURAL STIMULATION

CROSS REFERENCE TO RELATED APPLICATIONS

This application is a national stage of PCT Patent Application No. PCT/US2018/014724, entitled "Electrode Agnostic, Supply Variant Stimulation Engine for Implantable Neural Stimulation" to Rozgic et al., filed Jan. 22, 2018, which claims priority to U.S. Provisional Application No. 62/448,853, entitled "Electrode Agnostic, Supply Variant Stimulation Engine for Implantable Neural Stimulation" to Rozgic et al., filed Jan. 20, 2017, the disclosures of which are incorporated by reference herein in their entirety.

STATEMENT OF FEDERALLY SPONSORED RESEARCH

This invention was made with government support under Grant Number W911NF-14-2-0043, awarded by the U.S. Department of Defense, Defense Advanced Research Projects Agency. The government has certain rights in the invention.

FIELD OF THE INVENTION

The present invention generally relates to neuromodulation systems and in particular to programmable electrode agnostic stimulation engines.

BACKGROUND

There has been great interest in the neuroscience community in decoding the functioning of the brain. Among the various methods used, analysis of the recordings of the electrical activity of neurons has been among the most important tools available. These recordings can be indispensable for understanding and diagnosing neurological disorders like epileptic seizures, in the creation of brain-machine interfaces, and for neuro-prosthetic technologies to aid paralyzed patients. Further, modern neuroscience is attempting to "close the loop" with the brain, by stimulating specific areas using current pulses, and recording neuronal responses to learn and adapt the stimulation patterns. For example, it has been demonstrated in a limited number of patients that stimulating certain regions of the entorhinal cortex of the brain could improve memory function.

SUMMARY OF THE INVENTION

Neuromodulation systems and in particular programmable electrode agnostic stimulation engines in accordance with various embodiments of the invention are disclosed. In one embodiment, an integrated circuit includes at least one contact, and a stimulation engine circuitry that includes: a digital control unit (DCU) that activates the stimulation engine during active stimulation, a current mirror comprising two feedback loops including a first feedback loop with positive feedback (PF) and a second feedback loop with a negative feedback (NF), and a high-voltage adaptive rail ($V_{DD}/V_{SS}$) to accommodate voltage drops across high electrode impedances.

In a further embodiment, the first feedback loop with positive feedback includes an error amplifier $A_1$ and transistors $M_3$ and $M_1$.

In still a further embodiment, the second feedback loop with negative feedback includes the error amplifier $A_1$ and transistor $M_3$.

In a further embodiment again, the integrated circuit further includes adaptive closed-loop 4-stage charge pumps that provides supply rails $V_{DD}/V_{SS}$.

In yet another embodiment, the PF is synchronized with an input signal and is determined as a positive loop gain (LF) within a feedback loop.

In yet a further embodiment again, the integrated circuit further includes an extra NF that includes another operation amplifier $A_2$, wherein a plus terminal of amplifier $A_2$ is attached to a bias voltage, $V_B$ to facilitate the $V_{out}$ swing increase of the mirror by shielding the input of $A_1$.

In a further embodiment again still, the integrated circuit further includes cascode PMOS/NMOS amplifiers that control voltage-levels close to $V_{DD}/V_{SS}$ In another further embodiment again still, the integrated circuit further includes a local switch matrix (LSM) for biphasic control and post-stimulation active charge balancing.

In yet another embodiment again, the DCU configures an output of high voltage generators to produce stimulation power supplies $V_{DD}$ and $V_{SS}$.

BRIEF DESCRIPTION OF THE DRAWINGS

FIG. 14 shows measured simultaneous current stimulation waveforms in accordance with an embodiment of the invention

DETAILED DESCRIPTION

Figure 1:
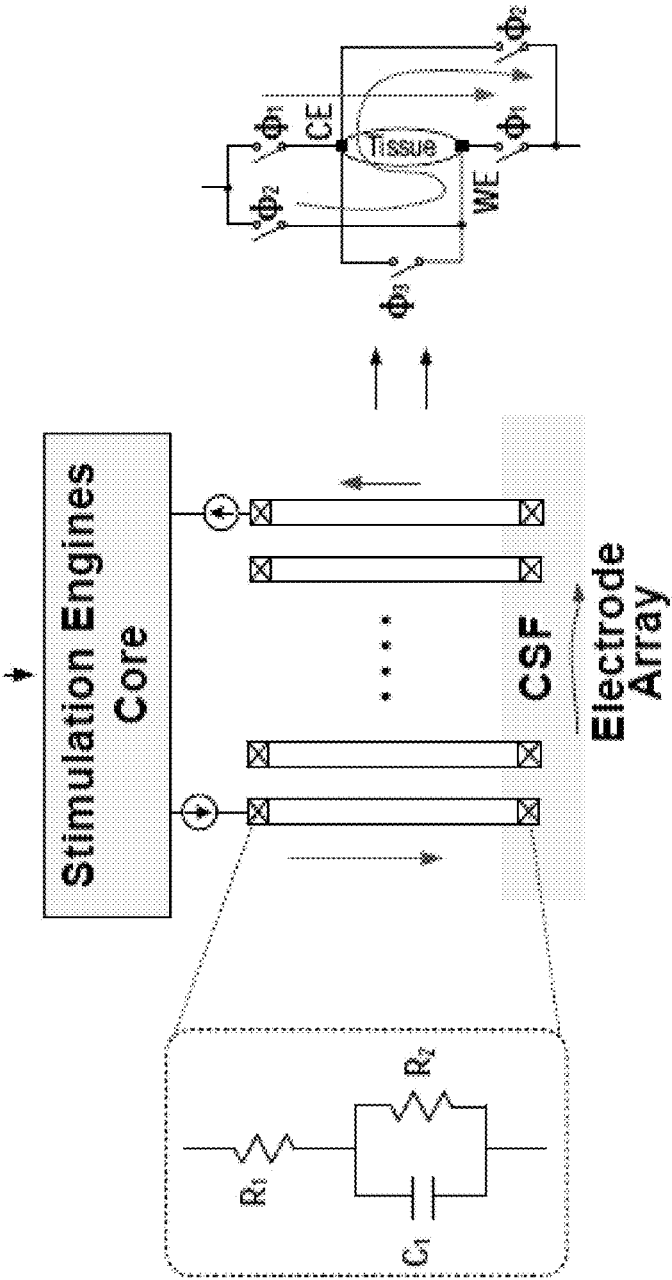
FIG. 1 illustrates an electrode-tissue model in accordance with an embodiment of the invention.

Turning now to the drawings, neuromodulation systems in accordance with various embodiments of the invention are illustrated. In many embodiments, in order to support different types of electrodes and a big range of stimulation current, the neuromodulation system provides a stimulation mechanism that is not electrode dependent. In several embodiments, the stimulation mechanism can account for "capacitive-looking" electrodes, extending the bipolar on-chip headroom of a CMOS stimulator. Accordingly, many embodiments provide a universal electrode agnostic stimulation engine that is fully programmable and which supply rails are variable to further save power. In several embodiments, during the simultaneous, multichannel, differential stimulation, the neuromodulation system provides superior current matching and makes concurrent stimulation and sensing possible.

To support simultaneous multi-channel, electrode agnostic stimulation, many embodiments use a very high output impedance current source/sink for a wide range of stimulus currents. In many embodiments, these features are possible due to the employment of feedback loops (negative and positive) used in the circuit. In particular, many embodiments of the neuromodulation system use a current mirror that includes two feedback loops: first with a positive feedback (PF) and second with a negative feedback (NF). In many embodiments, PF is always synchronized with the input signal and can be determined as a positive loop gain (LG) within a feedback loop. In many embodiments, the neuromodulation system includes an extra NF that includes another operational amplifier can be added in the circuit. In many embodiments, folded cascode PMOS/NMOS amplifiers are employed to enable proper loop operation at voltage-levels close to $V_{DD}/V_{SS}$. Neuromodulation systems in accordance with various embodiments of the invention are described in detail below.

Introduction

Neuromodulation, e.g. deep-brain stimulation (DBS), can provide symptomatic relief to neurological disease by emitting pulses to overcome abnormal brain activity. It is efficacious in Parkinson's disease and other movement disorders, which are anatomically focal, where open-loop stimulation on just one contact is sufficient. The same technology doesn't show therapeutic benefit in network-scale indications such as depression or Alzheimer's disease, where a more precise localization as well as distributed sensing and stimulation are necessary. Since neurological conditions could stem from many brain regions, a modular neural interface with higher channel count can be desirable. Also, continuous open-loop stimulation can be harmful and it can lose efficacy over time because of the changes in the brain. Therefore, closed loop control can be desirable to understand the basic science of a disease. A closed loop system may require concurrent stimulation and sensing capability, where stimulation parameters can be adapted based on neural features extracted from the sensed data. Such a closed loop approach can significantly enhance therapeutic efficacy, minimize the undesirable outcomes, and improve the understanding of hidden brain dynamics.

As an important part of neuromodulation (NM) units, neural stimulators play a significant role in most every neural treatment. In general, stimulator power dominates the overall NM power. Also, stimulator IC design is generally driven by electrode performances (e.g., impedance, size of contacts, among various other constraints). Moreover, electrode impedance can vary in time.

Types of Neural Stimulation and Biphasic Current Pulses

Neural stimulation can be delivered as a train of controlled current pulses, which are usually zero-mean, into specific brain regions to modulate brain activity. Stimulation may be performed using techniques such as (but not limited to) a neural probe, or micro-electrode array, which serves as an interface between neurons and the electronic circuitry. As a first order approximation, an electrode-tissue model can be depicted as it is shown in FIG. 1, where $R_1$ is the sum of Faradaic charge transfer resistance and trace resistance, $C_1$ models double layer capacitance, while $R_2$ depicts so called Warburg impedance. For all practical reasons during stimulator design, $R_2$ can be neglected.

Figure 2:
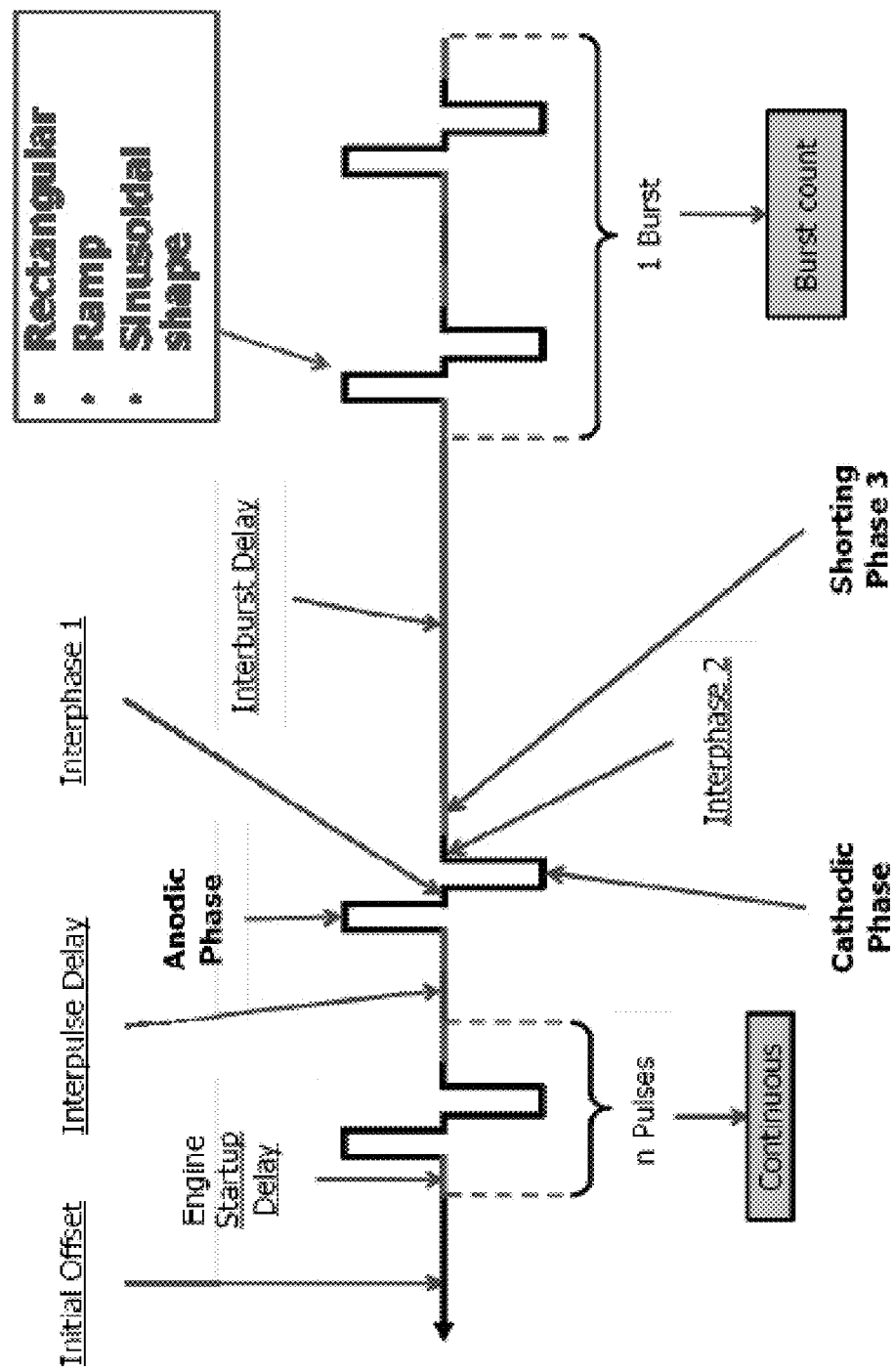
FIG. 2 illustrates different amplitude and timing parameters that can be set during active stimulation in accordance with an embodiment of the invention.

FIG. 2 illustrates different amplitude and timing parameters that can be set during active stimulation. Also, different kinds of stimulus waveforms can be adopted, depending on the application. The physiological response generated by the stimulation is typically directly dependent on the waveform. Among different pulse shapes that can be employed, biphasic current pulses may be preferred due to the charge balancing property. During biphasic stimulus, anodic phase increases the likelihood of positive charge delivery to the tissue, while cathodic phase provides a negative charge delivery. Inter-phase delay separates the cathodic (CP) and anodic pulse (AP) so that the AP typically does not change the effect of the CP. Ideally, these two charge amounts should be equal, so that after one bi-phasic pulse, there is no remaining charge in the tissue. Since the ideal matching for all practical reasons is not possible, to ensure safe operation, the residual charge may need to be removed. Hence, these two phases are followed with shorting phase, in which electrodes are shorted to the gnd or some other DC-level and all residual charge is removed. Switches $\Phi_1$, $\Phi_2$, $\Phi_3$ can be responsible for the bi-phasic stimulation control. Duration of the shorting phase may be directly proportional to the $R_1$-$C_1$ constant of the electrode.

Safe operations of the stimulator is necessary, otherwise tissue damage may occur. Tissue damage can be induced in several different ways, including: i) heat dissipation whereby the implanted hardware releases too much heat that can effectively cause the temperature to rise at the electrode-tissue interface, currently the FDA safe limit is <2° C.; ii) charge imbalance during stimulation; iii) excessive charge injection, whereby the size (cross-section) and the electrode material dictates the limit for the safe charge density.

Neural stimulation can be monopolar and differential. In monopolar stimulation, usually there are several stimulating electrodes and one return electrode which plays the role in the charge recovery. This method shows shortcomings if precise stimulus localization is necessary. FIG. 1 illustrates an example of differential stimulation, where a pair of electrodes is used at each stimulation cite; the current is pushed from the current source through the working electrode (WE) and it closes the loop through CSF (conductive cerebrospinal fluid), counter electrode (CE) and current sink. Differential stimulation can be a preferable method during the simultaneous stimulation in which multiple stimulus drivers are used for concurrent stimulation on several electrode pairs. Also, differential stimulation may prevent large common mode swings.

There are several types of neural stimulation. Each type brings different types of drawbacks and benefits. In particular, Voltage Current Stimulation (VCS) can provide power efficient stimulation, but since electrode impedance may vary over time and position, the charge balancing can be problematic. Recently proposed Switched-Capacitor Stimulation (SCS) offers a good tradeoff between safety and efficiency, but SCS can require a big number of off-chip capacitors and typically cannot be used in multi-channel, simultaneous stimulation since current splitting among channels is undesirable. As a widely used method in neural stimulation, current-controlled stimulation (CCS) offers an accurate charge control, but it can reduce power efficiency because of the voltage drops across current mirrors (sink/source) in the output stage of stimulators.

Different applications may need different types of electrodes (e.g., deep brain stimulation (DBS), epiretinal stimulation, among others); macro and micro electrode contacts show big range in tissue-electrode capacitances—from a few nF to a few μF. To support various electrodes and to allow a wide range of stimulation currents, it may be important to have a stimulation mechanism that accounts for the "capacitance-dominant" electrodes and extends the on-chip voltage headroom for the stimulation circuitry. Since many embodiments of the neuromodulation system design provide simultaneous, multichannel and electrode agnostic stimulation engines that may compensate for the variability of electrode-tissue impedance, efficient CCS design is a preferable choice.

Design Settings

Many embodiments of the neuromodulation system target a next generation neural interface that is minimally invasive and addresses the demands for limited area and power. Furthermore, many embodiments of the neuromodulation system provide real-time, full duplex communication during concurrent stimulation and recording of neural signals. Further, many embodiments of the neuromodulation system provide a modular approach and scalable architecture that should allow gathering data from a grid of NM implants.

In a particular neuromodulation system developed in a first stage, a wired supplied 32-channel module together with 4-driver-to-32-channel fully flexible stimulation module can deliver up to 3.1 mA per engine in a 128-channel implantable closed-loop system. In a second stage, the capability was scaled up to 64 channels, with stimulation to include 8 drivers (A-H, 5.1 mA each), supported with highly efficient wireless power and data link. In many embodiments, this interface can be integrated together with implantable electrode arrays and packages into 64-channel modules that may be further assembled into a 256-channel system.

System Architecture

Figure 3:
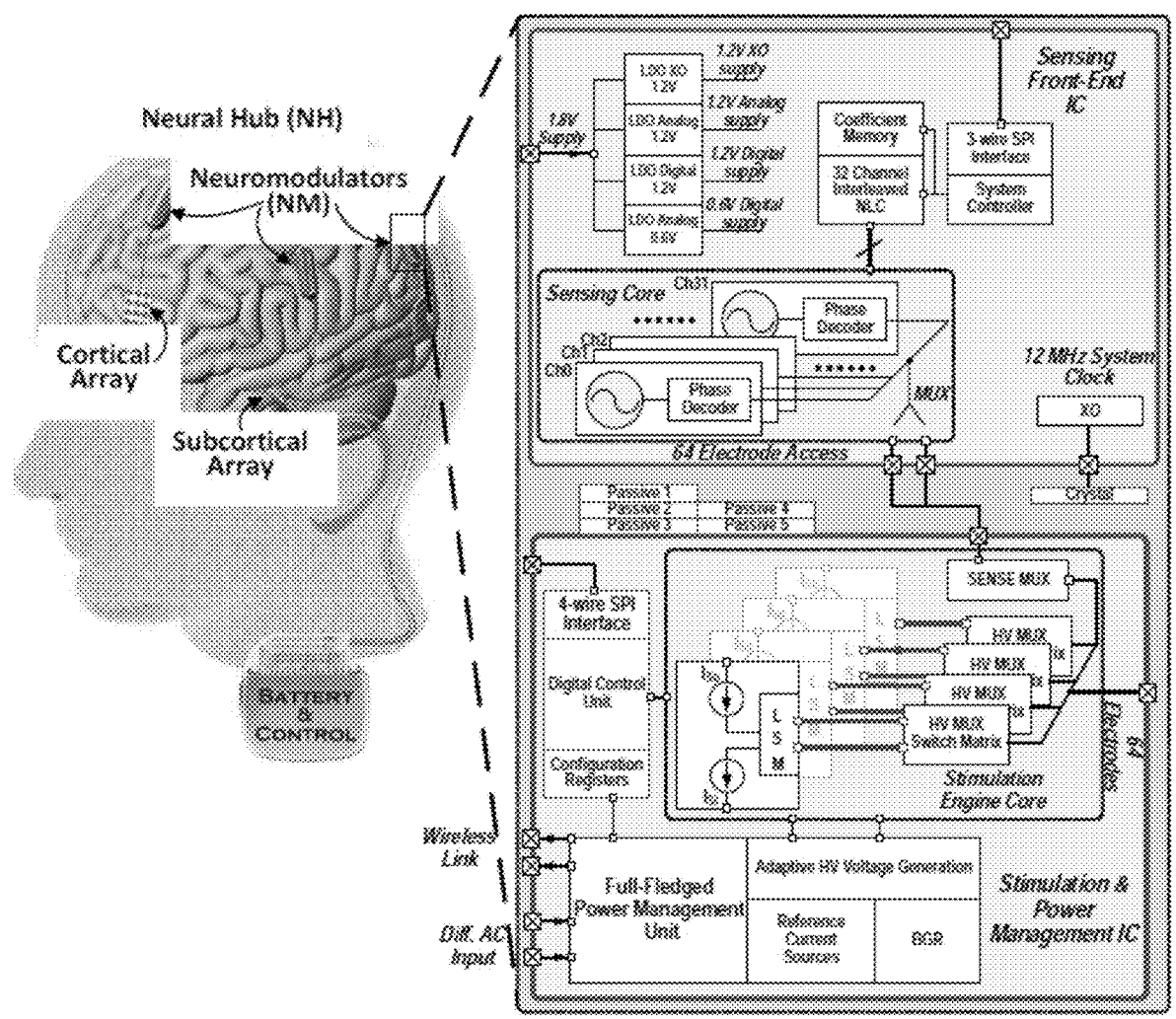
FIG. 3 illustrates an implantable neuromodulation system for deep brain stimulation treatment in accordance with an embodiment of the invention

In many embodiments, there are several primarily targeted applications. The first one considers an implantable neuromodulation system for DBS treatment. FIG. 3 illustrates an implantable neuromodulation system for DBS treatment in accordance with an embodiment of the invention. As illustrated in FIG. 3, the system includes several NM "smart lead" units, each with stim and sense ICs assembled to cortical or sub-cortical leads using high-density feedthroughs. In many embodiments, the Neural Hub (NH) serializes data from 32-ch/64-ch NMs and communicates with a control module in the chest. The second one may extend the capabilities of the first one and enables wireless power transfer (WPT) which is usually the only way of supplying fully implantable medical devices and plays an unavoidable power solution for cochlear implants and retinal prosthesis. Many embodiments of the neuromodulation system provide an implant for restoring active memory, placed at the temporal lobe that besides the NM core provides also the wireless data link. Although FIG. 3 illustrates a particular implantable neuromodulation system architecture for DBS treatment, any of a variety of architectures may be utilized as appropriate to the requirements of specific applications in accordance with embodiments of the invention.

Stimulation Engine

Figure 4:
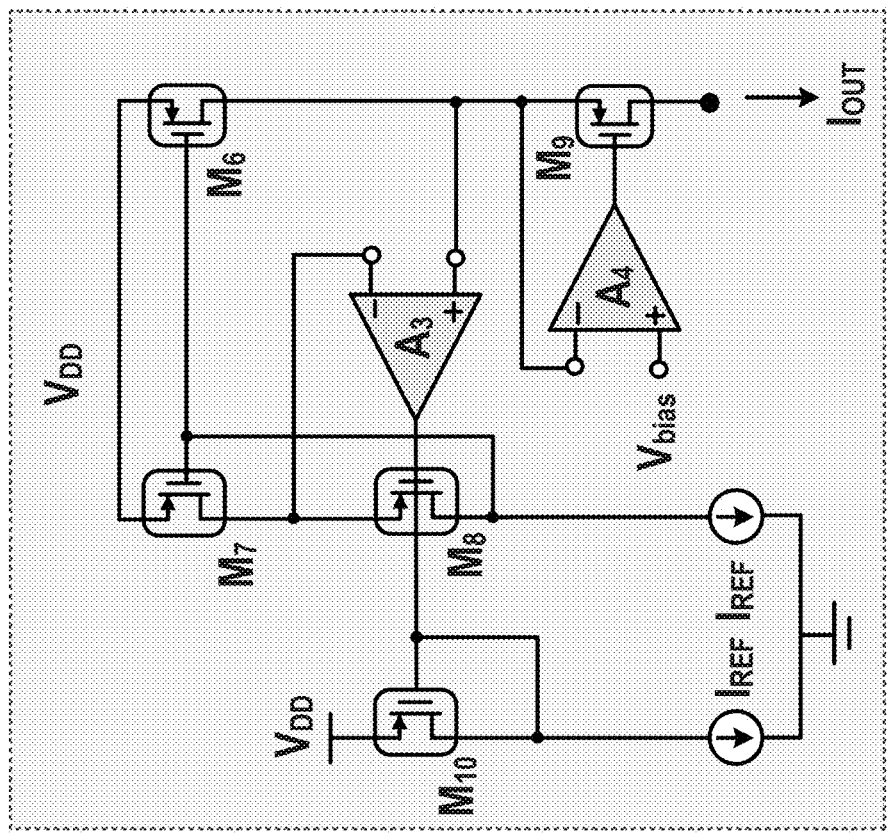
FIG. 4 illustrates a core of a stimulation engine (SE) in accordance with an embodiment of the invention.
Figure 4:
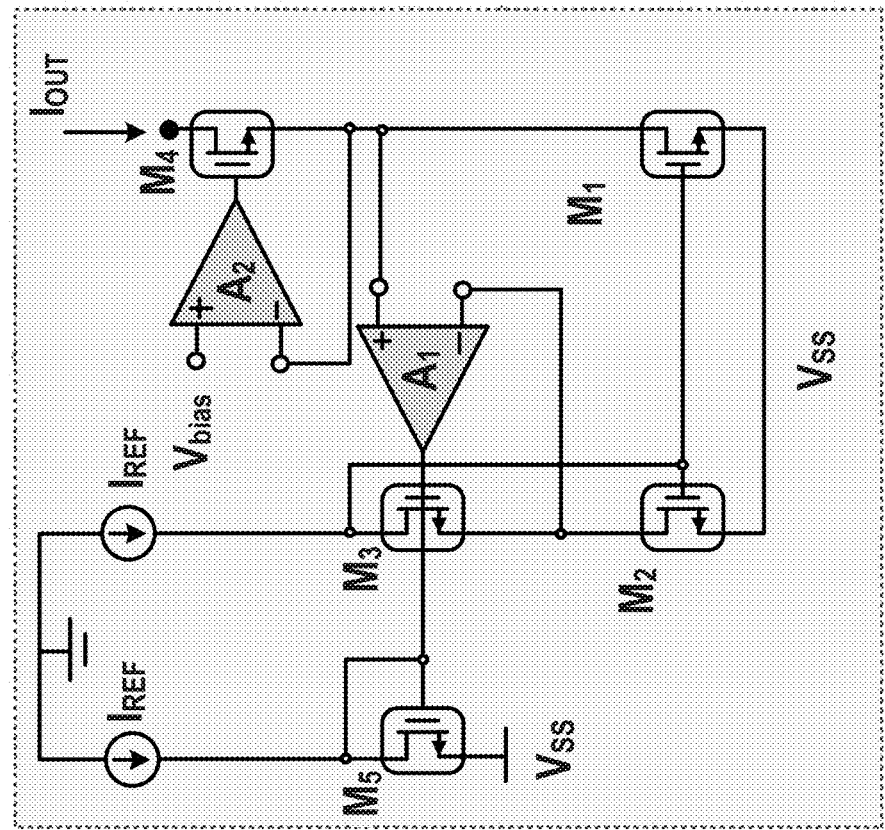

In the core of every stimulation engine (SE), many embodiments include a current source and/or current sink depending on the types of neural stimulation. The electrode-tissue impedance varies over time and its value may also depend on electrode placement in the nerves. Also, different electrodes may have different impedances depending on the material that they are made of and depending on the size of contacts (e.g., range ~100's Ω–1 MΩ). To support simultaneous multi-channel, electrode agnostic stimulation, many embodiments may need a very high output impedance current source/sink for a wide range of stimulus currents. Furthermore, the current mirrors should have a high output compliance to compensate the source/sink additional voltage headroom requirements in CCS, so that most of the rail-to-rail voltage can be dedicated to the output electrode pair (differential voltage). FIG. 4 illustrates a core of a stimulation engine (SE) in accordance with an embodiment of the invention that includes a very precise, ultra-high output impedance and high-compliance current mirror for the source/sink as part of the SE. In many embodiments, these features are possible due to the employment of feedback loops (negative and positive) in the circuit. This high-voltage current mirror can be superior in harvesting super-high output impedance, high accuracy and high compliance achieved by any stimulation engine.

As illustrated in FIG. 4, the current mirror can include two feedback loops: first with a positive feedback (PF) (including an error amplifier $A_1$ and transistors $M_3$ and $M_1$) and second with a negative feedback (NF) ($A_1$ and $M_3$). In many embodiments, PF can be synchronized with the input signal and can be determined as a positive loop gain (LG) within a feedback loop. Keeping only amplifier $A_1$ and transistors $M_3$ and $M_1$ as a current mirror may limit the output voltage by a single $V_{DSAT}$. But this structure can have a serious drawback—for the increased values of output voltage, $M_3$ goes into its linear region, since the aspect ratio of $M_2$ and the input current source dictates the DC value of $V_{G2}$. The output voltage is bounded:

$$V_{OUT} \leq V_{G2} - V_{DSAT3}. \tag{1}$$

To prevent this, in many embodiments, an extra NF that includes another operational amplifier ($A_2$) can be added in the circuit. The plus terminal of amplifier $A_2$ can be attached to a bias voltage, $V_B$. This would imply that the voltage at the plus terminal of $A_1$ is going to be set to a wanted value and enlarging values of $V_{OUT}$ may not push the loop run by $A_1$ to its bound. Attaching the plus terminal of amplifier $A_2$ to a $V_B$ may facilitate the $V_{OUT}$ swing increase of the mirror by shielding the input of $A_1$. From the small signal analysis, the output resistance of the current mirror can be expressed as $$R_{OUT} = r_{o4}g_{m4}r_{o1}g_{m2}A_2R_{IN}, \tag{2}$$

where $R_{IN}$ represents the input resistance of the mirror. This clearly shows that amplifier $A_2$ also contributes to the boosted output resistance. The output resistance may be boosted and the voltage compliance is expected to be approximately $V_{DD} - 2V_{DSAT}$. In many embodiments, folded cascode PMOS/NMOS amplifiers are employed to provide the proper loop operation at voltage-levels close to $V_{DD}/V_{SS}$. Although FIG. 4 illustrates a particular circuit architecture of a core of an SE, any of a variety of architectures may be utilized as appropriate to the requirements of specific applications in accordance with embodiments of the invention.

Figure 5:
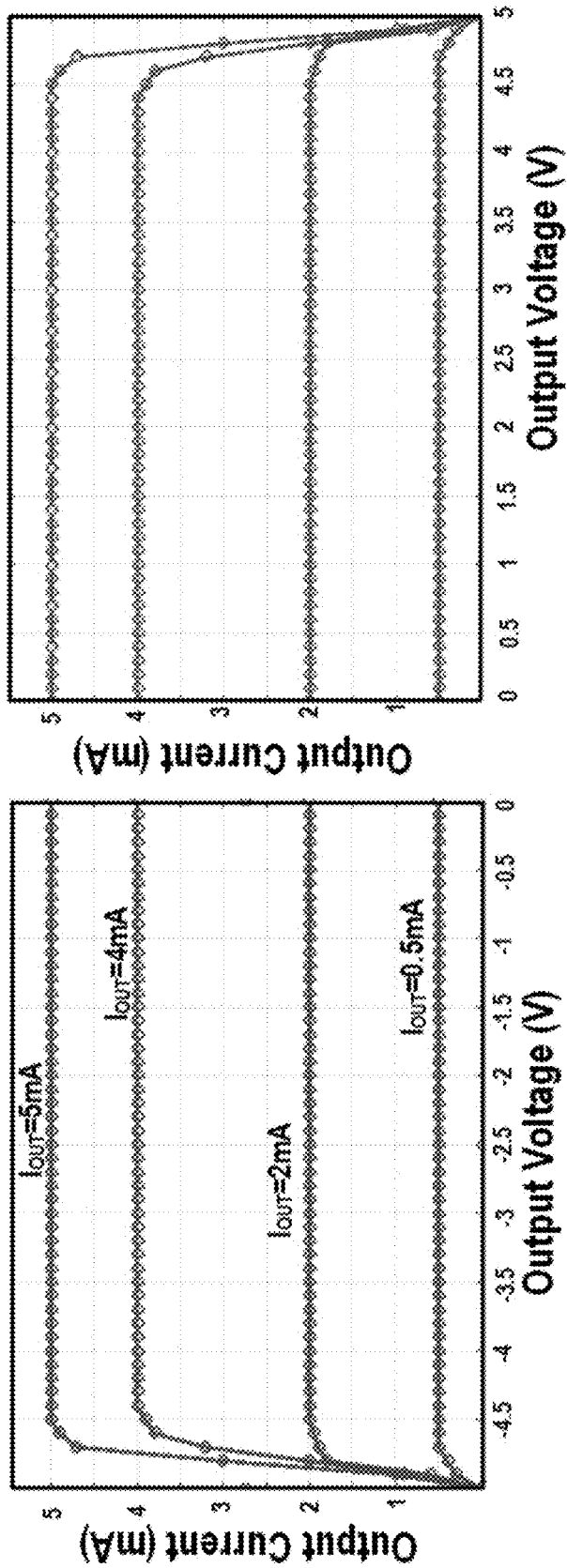
FIG. 5 illustrates measured DC output characteristic for current source/sink across a wide range of output currents in accordance with an embodiment of the invention.

FIG. 5 illustrates measured DC output characteristic for current source/sink across a wide range of output currents in accordance with an embodiment of the invention.

Figure 6:
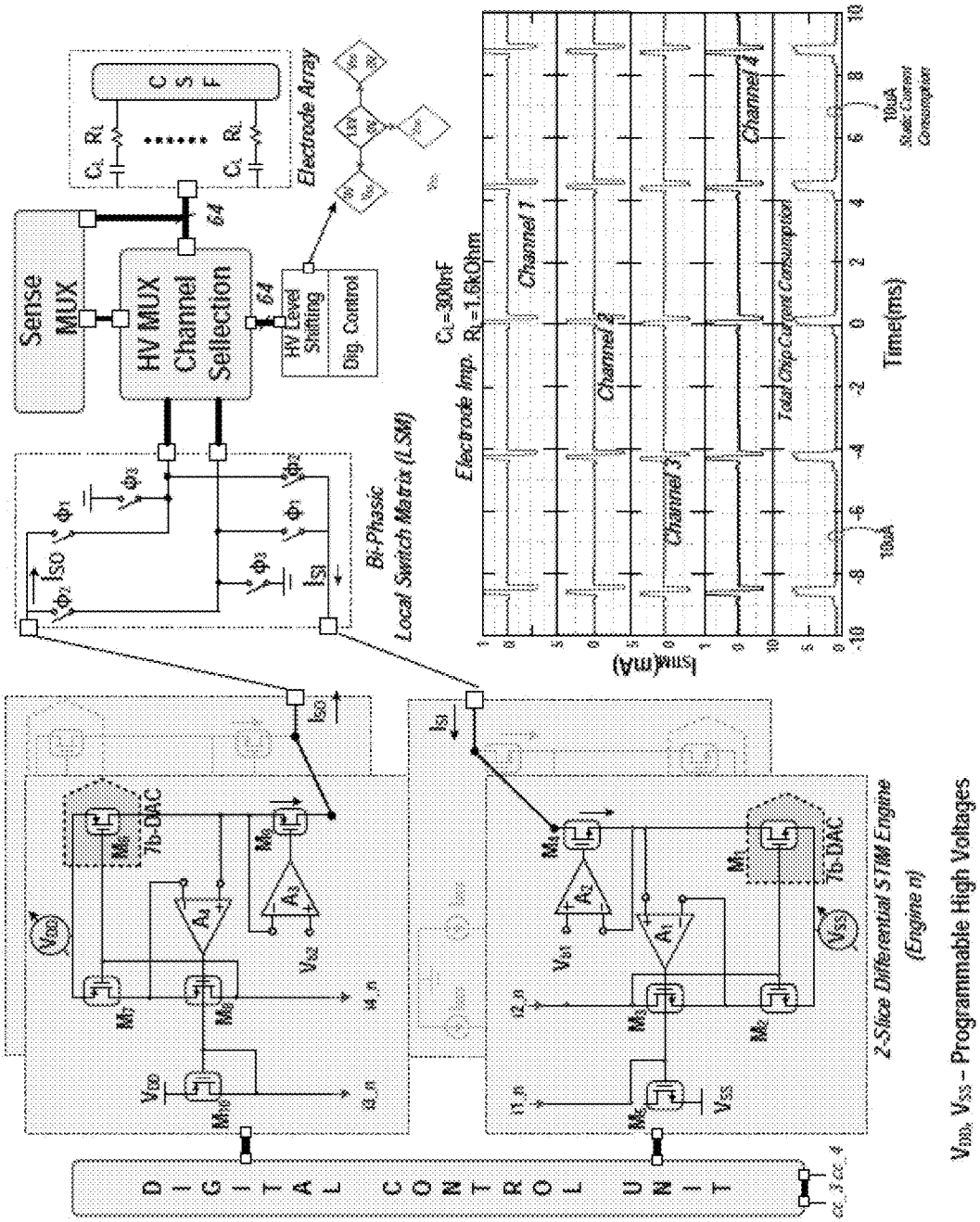
FIG. 6 illustrates an example of a complete Stimulation Engine architecture in accordance with an embodiment of the invention.

FIG. 6 illustrates a complete Stimulation Engine architecture in accordance with an embodiment of the invention. As illustrated in FIG. 6, Digital Control Unit (DCU) may activate the STIM engine during active stimulation. The STIM engine includes two driver slices, each with a 7-bit current source/sink for differential stimulation (to reduce artifacts), with integrated high-voltage (HV) level shifters (LS). By employing current mirrors, the output impedance of the current mirror can be boosted to 100's MΩ–1 GΩ. This architecture increases the likelihood of accurate current matching even for the large voltage swings (e.g., 94% $V_{rail-to-rail}$) at the electrodes.

Figure 7:
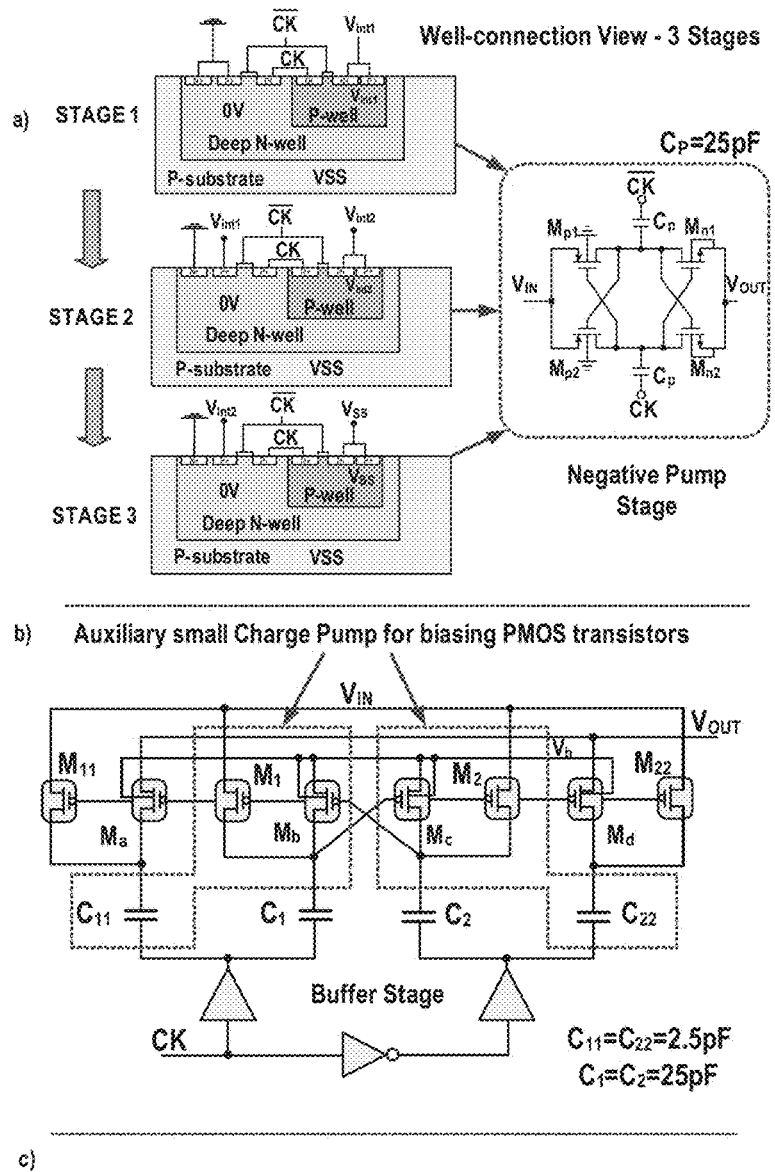
FIG. 7 illustrates an architecture of a charge pump in accordance with an embodiment of the invention.
Figure 7:
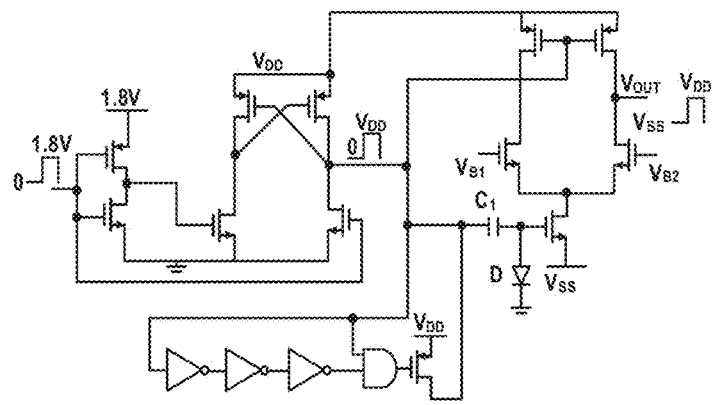

In many embodiments, the shape, amplitude, various timing parameters and SENSE/STIM MUXs can be configured by the DCU and updated on-the-fly. The output of the STIM engine may be connected to the local switch matrix (LSM), which is employed for the biphasic control and post-stimulation active charge balancing. Any residual charge on the electrodes can be cancelled out by shorting. In many embodiments, the HV channel-selection MUX provides a fine spatial granularity (8:64 MUX with integrated HV LS), for a multitude of stimulation sites. Since the control signals typically have a 1.8V level and HV STIM engine may require unipolar-to-bipolar voltage conversion, many embodiments employ a specific architecture, an exemplary embodiment of which is illustrated in FIG. 7 item c, for the HV Bipolar Level Shifting. In many embodiments, the STIM MUX determines the sense-IC accessibility to electrodes and protects the sense-IC from voltage overstress, since the sense-IC is typically implemented using lower node technology.

Figure 8:
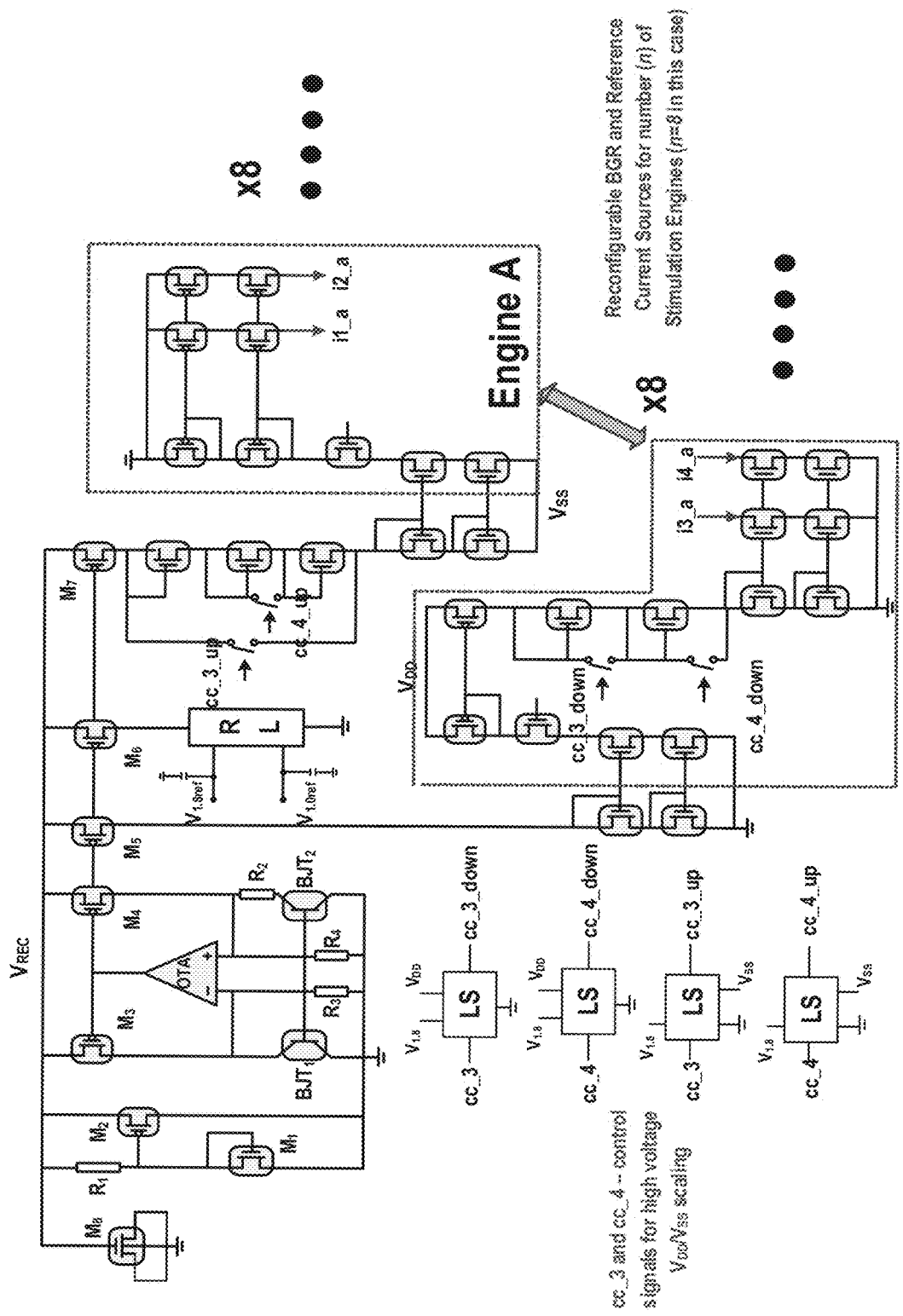
FIG. 8 illustrates a reconfigurable BandGap Circuit and Reference Current Source in accordance with an embodiment of the invention.

Power efficient stimulators may be necessary in energy-limited systems. The stimulator engine can dissipate significant power at its output stage, especially when it delivers small currents. This can be the main drawback of a system that implements CCS. To additionally save the power, in several embodiments, a high-voltage adaptive-rail ($V_{DD}/V_{SS}$) is provided to accommodate voltage drops across high electrode impedances. When the electrode sites are stimulating with specific current levels, DCU can configure (e.g., control bits cc_3, cc_4) the output of the high voltage generators to produce stimulation power supplies $V_{DD}$ and $V_{SS}$ according to the stimulation electrode needs (lower current—lower stimulation voltage and vice versa). An adaptive HV stimulation approach may prolong battery life up to 10×. At the same time, in many embodiments, a reconfigurable BandGap Circuit and Reference Current Source, as illustrated in FIG. 8, can be implemented in a manner that is relatively immune to $V_{DD}/V_{SS}$ changes.

Adaptive High Voltage Generator

As discussed above, power efficient stimulation in energy limited applications can be an imperative. Stimulators generally may require high voltage and high power dual supplies to support a wide range of stimulations currents and differential stimulations. Fully integrated High Voltage Generators (HVG) in multi-voltage systems with high power efficiency may be implemented.

Many embodiments provide a neuromodulation system designed with adaptive closed-loop 4-stage charge pumps, with a leakage reduction scheme, that can provide ±7.5V supply rails ($V_{DD}/V_{SS}$)–max 3.5× voltage conversion ratio.

Figure 9:
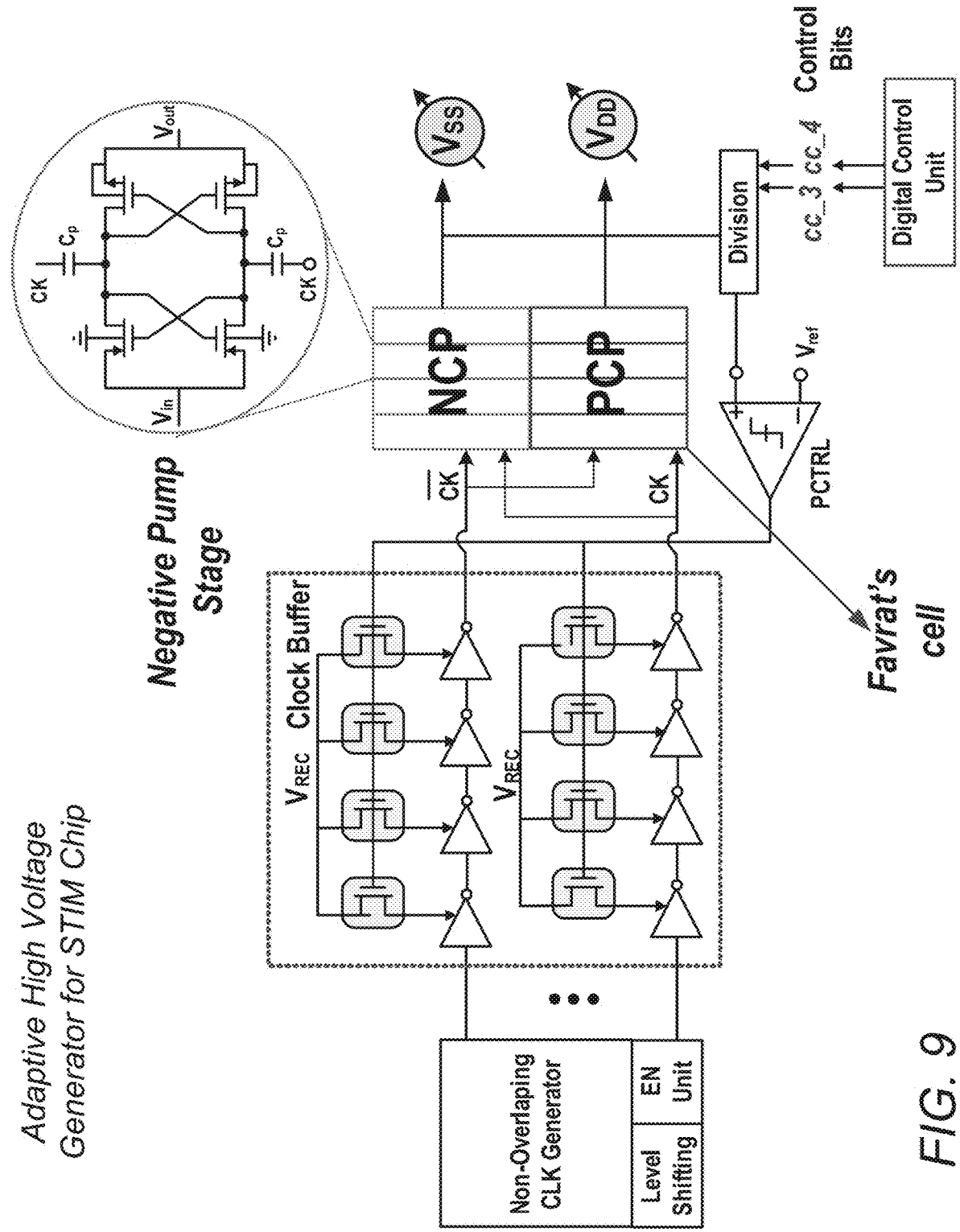
FIG. 9 illustrates a neuromodulation system designed with adaptive closed-loop 4-stage charge pumps with a leakage reduction scheme in accordance with an embodiment of the invention.

FIG. 9 illustrates a neuromodulation system designed with adaptive closed-loop 4-stage charge pumps with a leakage reduction scheme in accordance with an embodiment of the invention. Integrated charge pump efficiency may be improved by using a modified Pellicone's cross-coupled cell for the negative pumping stage and a Favrat's cell, as illustrated in FIG. 7 part a, for the positive pumping stage. Each Favrat's cell may use a small auxiliary charge pump structure for biasing a PMOS devices. The generation of negative voltages on the IC may be possible due to the triple-well process, as illustrated in FIG. 7 part b. In many embodiments, the bulk of the PMOS device is connected to gnd in order to prevent latch-up. The settling time of negative voltage generator (NVG) can be very fast due to the high frequency of operation (fs=20 MHz) and full integration of charge pumps. In many embodiments, the charge pump b performance is optimized to provide up to 1 mA of constant DC load current while maintaining a high efficiency.

To further increase energy savings, an efficient high voltage $V_{DD}/V_{SS}$ scaling may be employed. DCU can configure control bits cc_3, cc_4 to accommodate the outputs $V_{DD}$ and $V_{SS}$ of HVG at the optimal value which is sufficient for power efficient stimulation.

In the core of the HVG scheme there may be multiple pumping stages with non-overlapping clock generators and a feedback loop as shown in the embodiment illustrated in FIG. 9. The feedback loop may include the clock buffer and comparator that provides adaptive control signal. This feedback signal can be used to decide when the output voltage ($V_{DD}/V_{SS}$) of the HVG reaches a desired value. When that happens, the comparator may output the high signal (e.g. 1.8V), and the charge pump may stop pumping by disabling the clock buffer. Until the output voltage does not reach the targeted value, the output of the comparator is kept low. The main sources of the efficiency drop lie in the timing mismatch and in overlapped clock signals that can cause reverse current flow. To reduce reversion losses, many embodiments of the neuromodulation system are designed with a dedicated control scheme with an HV level shifting unit that increases the synchronization of the FETs (switches) so that they are not ON at the same time. This may enhance the power efficiency and by adding the filtered capacitors at the input of the comparator, the output voltage accuracy may be improved.

In this topology, the voltage drop across the stage is roughly equal to 2 $V_{DS}$, while the output voltage can be approximated as $$V_{OUT} \approx V_{IN} + N\left(\Delta V - \frac{I_{OUT}}{f_s C_f}\right), \quad (3)$$

where $$\Delta V \approx V_{sup} \frac{C_f}{C_f + C_{par}}$$

and $C_f$ is flying capacitor while $f_s$ denotes the switching frequency.

Figure 10:
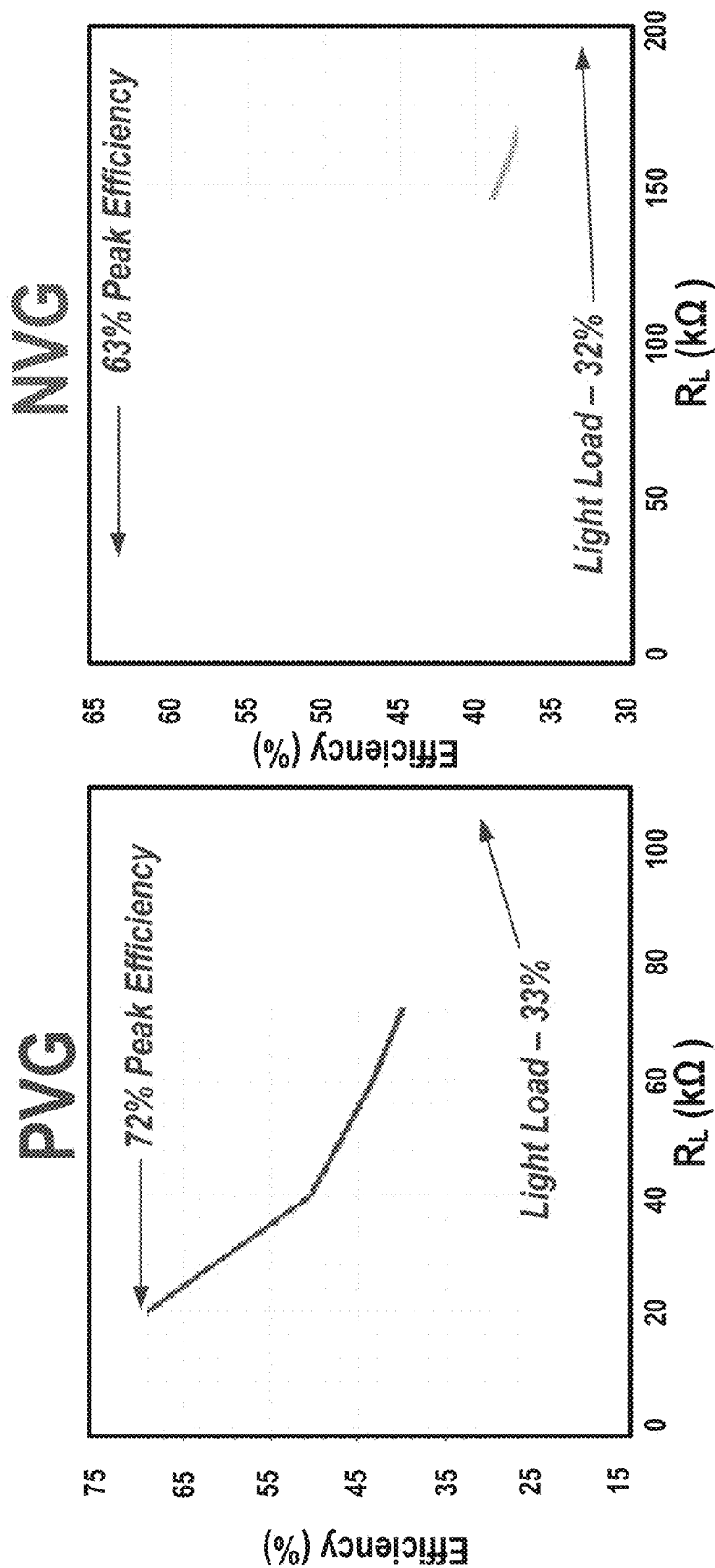
FIG. 10 illustrates power efficiencies for both positive and negative closed-loop charge pumps in accordance with an embodiment of the invention.

For an integrated implementation (flying capacitors on-chip) and mA output current capability to achieve a high voltage gain and high power efficiency, the switching frequency may need to be in 10's of MHz range. Power efficiencies for both positive and negative closed-loop charge pumps in accordance with an embodiment of the invention are illustrated in FIG. 10.

Another constraint may come from the stimulator requirement. During active stimulation, engines can drain 10's of mA of current from the high voltage supplies $V_{DD}/V_{SS}$. HVGs may not be able to provide that amount of current instantly. Accordingly, many embodiments provide a solution by having high value (e.g., 10 µF-20 µF) storage capacitances at the output of the HVG. The benefits of using these high value capacitances is twofold. First, output voltage ripple is proportional to $$V_{ripple} = \frac{I_{LOAD}}{f_s C_{OUT}},$$

hence it can be mitigated. Secondly, the voltage drop during the stimulation would be in order of several 10's of mV. Otherwise, a huge voltage drop could cause stimulator malfunction. Also, keeping $V_{DD}/V_{SS}$ within a safe range can be required for correct BGR and current mirror operation.

Figure 11:
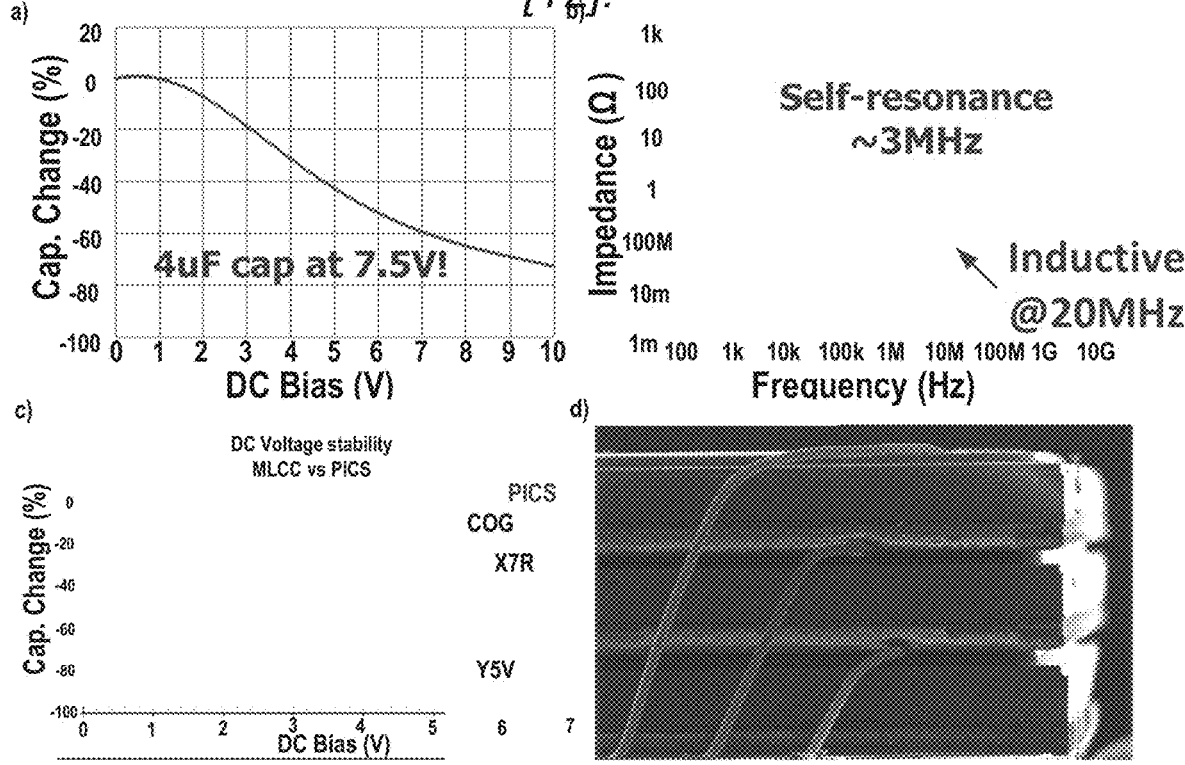
FIG. 11 illustrates a) Ceramic SMD Capacitance Drop with DC Voltage; b) self-resonance frequency of ceramic capacitors; c) comparison between ceramic SMD and Integrated Passive Capacitances; and d) stacked IPDIA capacitors as a compact energy source in accordance with an embodiment of the invention.

Apart from the necessity and benefits that introduction of external capacitances may bring into the design of neuromodulation systems, there are a few challenges that have to be considered. Medical-grade, ceramic SMD capacitors show capacitance degradation as the DC voltage across the capacitor increases, as illustrated in FIG. 11 item a. Also, ceramic SMD capacitor self-resonance frequency, for capacitance values in the µF order, can be up to a few MHz. Since switching frequency of charge pumps can be 20 MHz, clearly the external ceramic capacitors can show inductive property at that frequency, as illustrated in FIG. 11 item b. As a consequence, the output charge pump ripple, that can be expressed as $$V_{ripple} \approx L\frac{di}{dt} + ESR * i, \quad (4)$$

where $ESR=R_{pcb}+R_{chip\_wire}+R_{cap}$ denote the serial accumulated resistance, can reach several 100's of mV. Such a big ripple on supplies may be unacceptable and can cause the stability issues.

An elegant solution for the above problem may be to use Integrated Passive Device (IPD) devices. These devices show no capacitance degradation over the DC voltage stress. Also, an IPD's negligible serial inductance introduces a very small voltage ripple. FIG. 11c shows the comparison between an IPD and a ceramic external capacitor in accordance with an embodiment of the invention. Another factor that may play an important role in volume-limited, miniaturized applications is the size of external components. IPD may be a right choice when it comes to 3D passive integration as a top priority. Thickness of these capacitors can be between 80 µm and 100 µm while their capacitance density is 4 µF/mm³. An example of a cubic stack which can be stacked further on one of the ICs in accordance with an embodiment of the invention is illustrated in FIG. 11d. In many embodiments, stacking of the integrated storage capacitors may create more space on the assembly board and may reduce the overall size of implant-scale medical device.

Measurement Results

Figure 12:
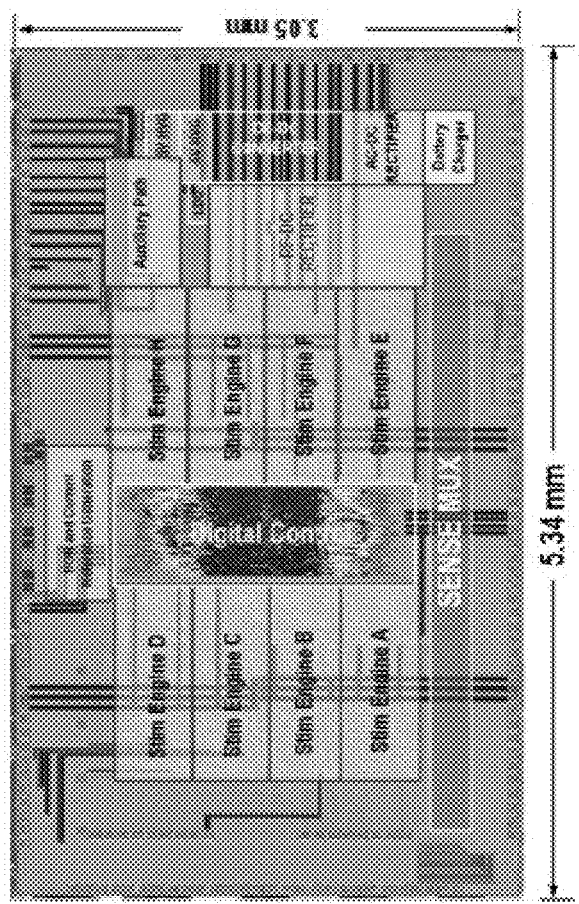
FIG. 12 illustrates two different STIM/PM ICs in accordance with an embodiment of the invention.
Figure 12:
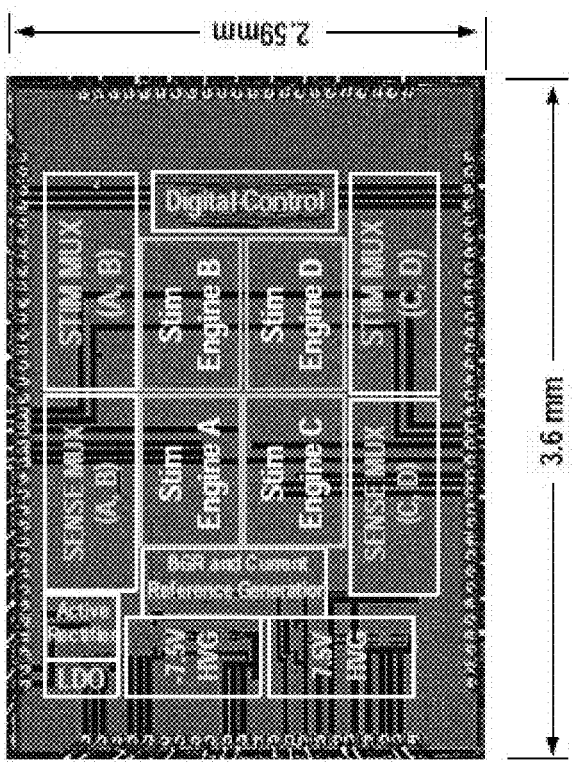

To demonstrate the functionality and performances of a neuromodulation systems in accordance with an embodiment of the invention, two different STIM/PM ICs, as illustrated in FIG. 12, were designed and experimentally verified—the first IC has 4 Stimulation Engines (SE) and can drive 32 stimulation cites with $V_{DD}/V_{SS}$ absolute maximum set to 7.5V/−7.5V. In the second version, the stimulator block includes 8 SE that can be individually programmed for monopolar/differential stimulation. Stimulation current, per engine, covers the range from 20 uA to 5.1 mA with 20 uA step. Programmability includes pulse shape, phase duration, full spatial selection, power control, etc. In many embodiments, engines are designed to be electrode agnostic.

In several embodiments, High Voltage STIM switching matrices are designed for 64 electrodes and STIM matrix provides a complex spatial resolution. The stim IC can be integrated in HV-180 nm CMOS to support a large voltage, while the sense IC can be implemented in 40 nm CMOS technology for reduced area and power of digital circuits.

Figure 13:
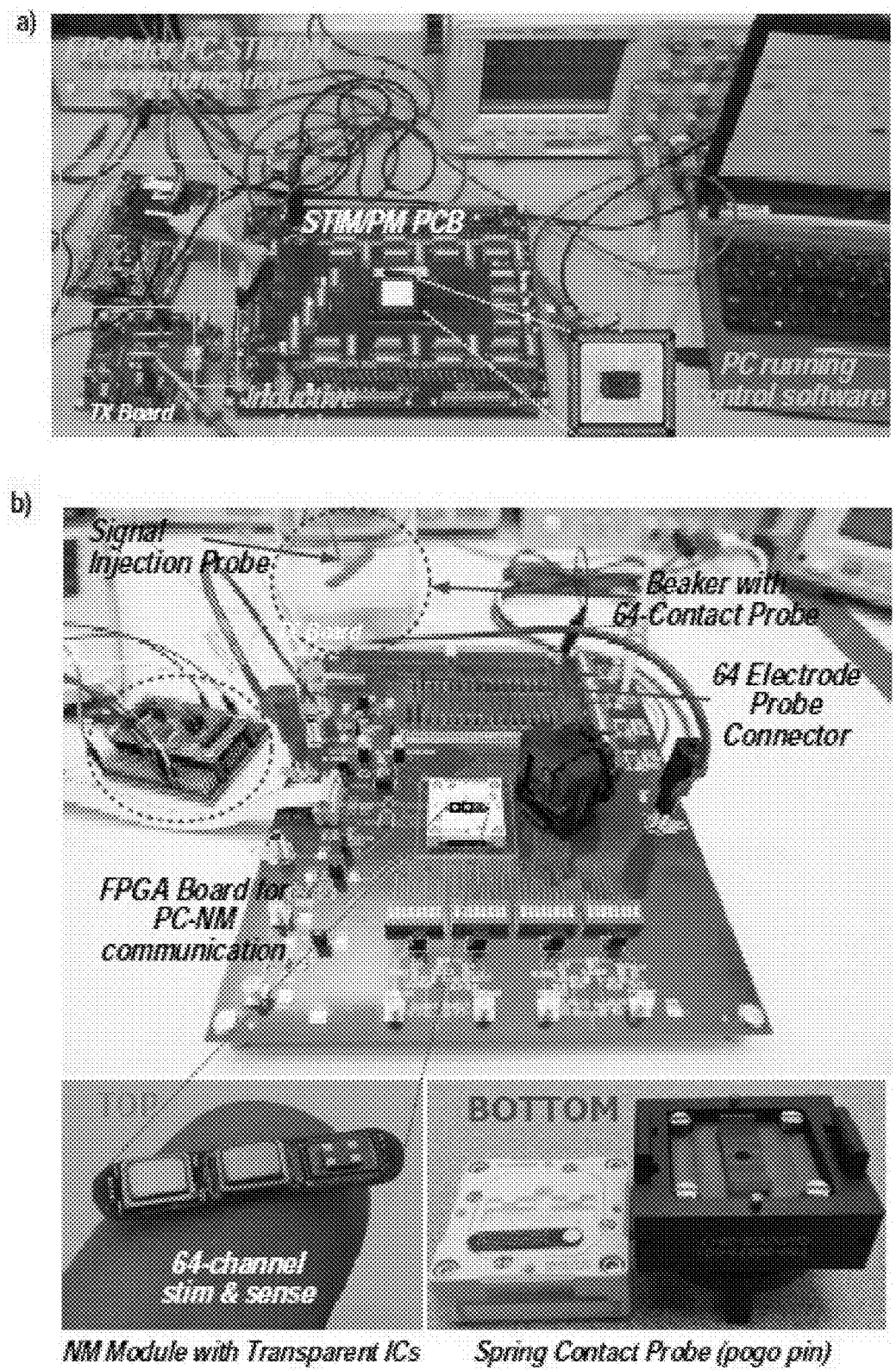
FIG. 13 illustrates a measurement setup in accordance with an embodiment of the invention.

A measurement setup in accordance with an embodiment of the invention is illustrated in FIG. 13. To evaluate the performances of the STIM/PM IC, a STIM test-bench board was designed as illustrated in FIG. 13 item a. The PC may be running a control software which sends the STIM and PM control parameters through the FPGA board toward the IC. To demonstrate the functionality of the NM unit, in-vitro measurements were conducted with a 64-electrode probe. FIG. 13 item b illustrates a test set-up that may be used to evaluate the system integrity under concurrent stim and sense in accordance with an embodiment of the invention.

Neuromodulation units may be designed and assembled for both versions of STIM/PM and SENSE ICs. The functionality of these two ICs can be supported by only a few passives—6 off-chip components are placed on the top side of the PCB. This unit may include stacked integrated IPDIA capacitors to further downsize the overall NM module. In many embodiments, the bottom side has the contacts for external connections—2 anti-phase AC power lines, 3-wire SPI interface, and 66 contacts for neural electrodes (1 'common', 1 'reference', and 64 targets). The overall NM capsule may be smaller than a US penny and occupies 552 mm³, while the inner volume where active electronics is placed may take 338 mm³−W=4.5 mm and L=22.5 mm, as illustrated in FIG. 13b, bottom.

This NM unit is small in size, which makes a high-channel count, closed-loop neuromodulation possible. The low-profile NM PCB assembly can be housed in a small package for on-the-skull implantation. This scheme can minimize the recording interference and reduce power in the cables for the NM. The distributed architecture may allow a clinician to adjust the number of NM satellites without modifying the system design.

In many embodiments, an advantage of this implantation scheme is the proximity of the sensors and stimulators to the electrode arrays, compared to the traditional approach where the pulse generator is in the chest area.

FIG. 14 shows measured simultaneous current stimulation waveforms in accordance with an embodiment of the invention. The stimulation waveform can be configured to have rectangular, exponential, sawtooth, triangle and sine pulse shape. During the power management start-up sequence, control signal EN_CP can be used to enable/disable HVG.

Many embodiments of the neuromodulation system implant show superior form factor and performance compared to the prior art. The improved performance may be a result of highly optimized designs and a modular approach that combines the best of different CMOS technologies. It also provides a unique ability to rapidly customize systems with varying channel counts via heterogeneous "chiplet" system-in-a-package assembly.

While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. An integrated circuit comprising,
   a multi-channel stimulation and sensing unit comprising a plurality of electrode contacts that provide concurrent stimulation and sensing;
   an on-chip power management unit;
   an on-chip electrode agnostic stimulation engine circuitry comprising:
      a digital control unit (DCU) that activates the electrode agnostic stimulation engine during active stimulation;
      a current mirror comprising two feedback loops including a first feedback loop with positive feedback (PF) and a second feedback loop with a negative feedback (NF); and
      a high-voltage adaptive rail ($V_{DD}/V_{SS}$) to accommodate voltage drops across high electrode impedances, wherein when the at least one contact is stimulating with a particular current level, the DCU configures an output of the high-voltage adaptive rail to produce stimulation power supplies $V_{DD}$ and $V_{SS}$ according to the at least one electrode contact impedance.

2. The integrated circuit of claim 1, wherein the first feedback loop with positive feedback comprises an error amplifier $A_1$ and transistors $M_3$ and $M_1$.

3. The integrated circuit of claim 2, wherein the second feedback loop with negative feedback comprises the error amplifier $A_1$ and transistor $M_3$.

4. The integrated circuit of claim 1, further comprising adaptive closed-loop 4-stage charge pumps that provides supply rails $V_{DD}/V_{SS}$.

5. The integrated circuit of claim 1, wherein the PF is synchronized with an input signal and is determined as a positive loop gain (LF) within a feedback loop.

6. The integrated circuit of claim 1, further comprising an extra NF that includes another operation amplifier $A_2$, wherein a plus terminal of amplifier $A_2$ is attached to a bias voltage, $V_B$ to facilitate the $V_{out}$ swing increase of the mirror by shielding the input of $A_1$.

7. The integrated circuit of claim 1, further comprising cascode PMOS/NMOS amplifiers that control voltage-levels close to $V_{DD}/V_{SS}$.

8. The integrated circuit of claim 1, further comprising:
   a local switch matrix (LSM) for biphasic control and post-stimulation active charge balancing.

9. The integrated circuit of claim 1, wherein the DCU configures an output of high voltage generators to produce stimulation power supplies $V_{DD}$ and $V_{SS}$.

* * * * *